United States Patent [19]

Trafford

[11] Patent Number: 5,403,226
[45] Date of Patent: Apr. 4, 1995

[54] LEAF CUTTER BEE NEST

[76] Inventor: Norman F. Trafford, General Delivery, Garland, Manitoba, Canada, R0L 0W0

[21] Appl. No.: 178,011

[22] Filed: Jan. 6, 1994

[51] Int. Cl.⁶ .............................................. A01K 47/00
[52] U.S. Cl. ............................................................ 449/4
[58] Field of Search .................... 449/4, 43, 44, 56, 61

[56] References Cited

U.S. PATENT DOCUMENTS

| | | | |
|---|---|---|---|
| 4,651,372 | 3/1987 | Schmidt | 449/44 X |
| 4,716,609 | 1/1988 | Norman | 449/4 |
| 4,765,007 | 8/1988 | McCarthy | 449/4 |

FOREIGN PATENT DOCUMENTS

| | | |
|---|---|---|
| 1260762 | 9/1989 | Canada. |
| 2007366 | 3/1991 | Canada. |
| 1288288 | 9/1991 | Canada. |

*Primary Examiner*—Robert P. Swiatek
*Attorney, Agent, or Firm*—Robert W. B. Bailey

[57] ABSTRACT

A molded plastic leaf cutter bee nest block, having opposed sides, opposed ends, and opposed faces, formed of expanded plastic beads, having nonstandard length, to accommodate more integrally molded round bee holes. The holes may be tapered, for ease of stripping. The sides may be reinforced for ease of handling, assembling, strapping, transport and storage. High density polystyrene blocks have improved product life, while the blocks, reinforced or otherwise are parasite resistant.

11 Claims, 2 Drawing Sheets

LEAF CUTTER BEE NEST

This invention concerns leaf cutter bee nests.

Although the invention is described and referred to specifically as it relates to specific structures of leaf cutter bee nests, it will be understood that the principles of this invention are equally applicable to similar structures and accordingly, it will be understood that the invention is not limited to such structures.

BACKGROUND OF INVENTION

Leaf cutter bees are becoming increasingly valuable in crop pollination. In contrast to honey bees, which fly long distances (several miles) and pollinate over wide areas, leaf cutter bees fly short distances (several hundred yards) and pollinate within a small area.

The continued advance of the Africanized "killer" bee, reaching Texas in 1993, and other unrelated honey bee disease problems, has raised potential long term concerns with honey bee pollination. Leaf cutter bees have become attractive potentially competitive alternative pollinators.

Accordingly leaf cutter bee pollination has generated and continues to generate substantial interest. Leaf cutter bees are solitary bees, unlike honey bees where only one female bee, the queen, lays fertile eggs, every female leaf cutter bee lays fertile eggs. The life cycle is quite different, the leaf cutter bees, female and male, overwinter as cocoons (pupae), emerging in the spring. The males who outnumber the females about two to one, mate with the females after emergence. The females then cut leaves and prepare cells in which they lay their eggs, which hatch into grubs, then become overwintering pupae or cocoons. The female typically prepares from ten to twenty-five egg cells, each with their cut leaf, which develop into cocoons (pupae), and later bees, of which about a third are female.

Commercially there are many systems of nesting leaf cutter bees, which have three separate components, the nest shelter, the mode of handling or installing the nests, and the nest structure itself. This invention is primarily concerned with nest structure.

PRIOR ART

The original commercial leaf cutter bee nest was probably a drilled wooden block, with holes typically roughly ¼ inch in diameter and roughly 3 to 4 inches deep, typically about 3¾ inches, to accommodate about ten completed cells, containing cocoons (pupae). The holes may be single ended (blind) or double ended (open).

Later these blocks were made from wooden laminates having semicircular holes gouged or planed by planers, having spaced planer knives or cutters. A wheel rested in a middle gap in a linear array of planar knives. Block width and bee hole spacing pattern were set by then technology, which became the standard. Stripping machines were developed to accommodate these blocks, which in turn led to standardized blocks, with double ended (open) holes, to fit standard stripping machines, which have two parallel rows of 30 pins each with a middle gap. The stripping machine pins push the bee cocoons (pupae), out of the holes.

This resulted in three arbitrary standardized restrictions, block width (roughly 1 foot, typically 11¾ inch), spacing of bee holes within rows (roughly somewhat less than 2/5 inch), and spacing of rows (roughly 2/5 inch). While other blocks can be designed, they must fit existing stripping machines as a practical matter.

As those skilled in the art are aware, block depth is more or less restricted by the stripping machines to about 4 inches. While it is true that longer pins may be employed the stripping machines mechanisms and construction would have to be varied to accommodate them. Shorter block depths are no problem, since the existing stripping machine pins can pass through them.

The bee cocoons require incubation at about 30° C. for about 20 to 30 days, before the bees hatch (emerge). In practice hatching (emergence) must coincide with crop bloom, for best effects. There is wide variety in incubating practices. Some leaf cutter bee keepers do not strip their nests, preferring to let the cocoons hatch and bees emerge naturally in the spring from the nest blocks. Under these circumstances, it is believed that natural heat generated by the emergence may cook or kill cocoons, at temperatures substantially above 30° C. If the bee holes are more than 3 inches deep, through the thickness of the block, then it is believed that the natural heat generated by emergence does cook or kill cocoons. If the bee holes are 3 inches or so deep it is believed that this does not occur. As with every matter relating to bees, including the very much studied honey bees, exactitude is lacking.

Plastic nest blocks have been developed to replace wooden nest blocks. One fairly well known variation is a molded plastic block, afterwards drilled similarly to its wooden predecessor. This particular block has no length restrictions, which is of considerable advantage, in handling. Its disadvantages may be summarized as follows, in order to successfully drill the block, its resistance to the drills must be low. Therefore the block is typically molded from styrofoam, expanded polystyrene beads and is of low density (about 1.8 pounds/cubic foot) which wears easily. Because the styrofoam is of low density the beads are expanded to greater size and subsequent precision drilling is difficult. The drills wander, the holes are not so well formed or aligned, and have ragged interiors, due to styrofoam beads being entirely removed during drilling, and also due to the drill hole penetrating the central space of expanded beads. The blocks thus lack integrity internally and because of their low density, and consequent softness, are fairly easily damaged during handling and stripping.

An alternative development produces molded blocks of styrofoam having molded holes, Canadian Patent 1,288,288, issued 3 Sep. 1991, to McCarthy, describing a vermiculite filled styrofoam. This is fairly restricted in size, for production reasons and are limited in practice to about 1500 holes or tunnels, or a length of some 21 inches, which also has considerable handling disadvantages. This product (uncertain as to any vermiculite content) sold by Beaver Plastics, additionally has 60 half holes, 30 at each end to accommodate the stripper pins, during stripping. Its density, to applicant's knowledge, is somewhere between 2 and 2½ pounds/cubic foot. Above about 2 pounds/cubic foot handling damage is noticeably less than at about 1.8 pounds/cubic foot, and decreases with increasing density. In current economic and commercial practice it appears that 2½ pounds/cubic foot is a possible practical upper density limit, although higher densities can be employed they are not of economic or commercial advantage.

It is general to combine these nest blocks to provide sufficient space for bees. As is shown in Canadian Patents 1,260,762 issued 26 Sep. 1989, to Norman, and 2,007,366, published 21 Mar. 1991, to Bjornson, et.al., surround kits are necessary to combine sufficient nest blocks in practice, and this is labor intensive and time consuming. Larger nest blocks, which would be longer and have more rows of bee holes, are desirable.

Although there is little uniformity in assembling nest blocks, the distribution of bees is fairly well understood, and one assembly of bee nests is required for every three to ten acres or so. These are provided within a single shelter, again of very wide design variation, and typically three or so assemblies of nest blocks are used. These depending on block size are strapped together similarly to Bjornson or Norman, and in the case of the molded hole blocks at least four are combined in one assembly. Both assembly and disassembly are labor intensive and time consuming.

It is an object of the invention to provide a bee nest having a larger molded plastic block with more molded holes than heretofore. It is a further object to provide a molded plastic bee nest having greater integrity (resistance to handling damage). It is a further object to provide a bee nest formed of molded plastic having reinforced sides. It is a further object to provide a bee nest having tapered molded holes. Other objects will be apparent to those skilled in the art from the following specification, accompanying drawings and appended claims.

DESCRIPTION OF THE INVENTION

In one broad aspect the invention is directed to a molded leaf cutter bee nest block, formed of expanded plastic beads, having opposed sides, opposed ends, and opposed faces. Round integrally molded bee holes extend from one opposed face to the other, which taper from a larger diameter in one said opposed face to a lesser diameter in the other said opposed face. This taper makes stripping much better, as the cocoons (or pupae) can be much more easily pushed out by stripping pins entering from the smaller end. Preferably the block includes more than about 1500 integrally molded bee holes, up to about 3600 or so. The larger diameter is preferably about ¼ inch and the lesser diameter is about 15/64 inch. 0.250 inch and 0.235 inch, respectively are especially preferred. More preferably the block is formed of expanded polystyrene beads, which in general contain no extra material beside the beads themselves. Preferably the opposed sides are reinforced by attached panels, which makes handling, assembling and strapping, as well as transport and storage much easier, as experience has amply demonstrated the sides are most prone to be damaged. Thus reinforcing the sides lengthens nest block life. It is markedly preferred that the block be formed of expanded polystyrene beads, having a density of at least about 2 pounds/cubic foot, conferring superior strength and a thicker more resistant skin, thus the block itself as opposed to its sides are made much more resistant to damage. The combination of this density and reinforced sides, which will considerably extend nest block life above either alone, is naturally especially preferred. Preferably the opposed sides are reinforced by attached panels, which are formed of resistant material. These may be wood products, such as plywood or particle board, and related materials, as those skilled in the art would be aware, which although serviceable are less preferred, because it is conceivable they may harbor parasites. Plastic may be utilized, such as masonite, formica, and related materials, as those skilled in the art would be aware, are preferred, since they are much less likely to harbor parasites.

In another broad aspect the invention is directed to a molded leaf cutter bee nest block, formed of expanded plastic beads, having opposed sides, opposed ends, and opposed faces. Round integrally molded bee holes extending from one opposed face to the other, the opposed sides are reinforced by attached panels, which increase ease of handing, assembling, strapping, transport, storage, and reduces the damage to which the sides are prone. Preferably the block includes more than 1500 integrally molded bee holes, more preferably up to about 3600 holes. Conveniently the block is formed of expanded polystyrene beads, more desirably it may have a density of at least 2 pounds/cubic foot.

A preferred commercial product of this broad aspect is formed of expanded polystyrene beads, having a standard depth of about between 3 and 4 inches depth, (3¾ inches preferred) a standard width of about 12 inches (11¾ inches preferred) and a nonstandard length of about 48 inches (47½ inches preferred). This accommodates 3540 integrally molded round bee holes and 60 end half holes in 120 rows. The holes extend from one opposed face to the other. Each row contains 30 holes, the rows of half holes form recesses in the block ends. Preferably the reinforcing panels are masonite. Desirably the nest block has a density of at least about 2 pounds/cubic foot. Most preferably the holes taper from about ¼ inch diameter in one said opposed face to about 15/64 inch diameter in the other said opposed face.

In practice the block density can be varied between about 2 and 2½ pounds/cubic foot, with about 2¼ pounds/cubic foot especially considered desirable.

As those skilled in the art would appreciate the molded blocks are parasite resistant, as are the masonite reinforcing panels. This together with ease of handling, assembly, strapping, transport, and storage makes the invention effectively superior in labor and time required, as well as having a longer life.

DESCRIPTION OF THE PREFERRED EMBODIMENTS

Figure 1:
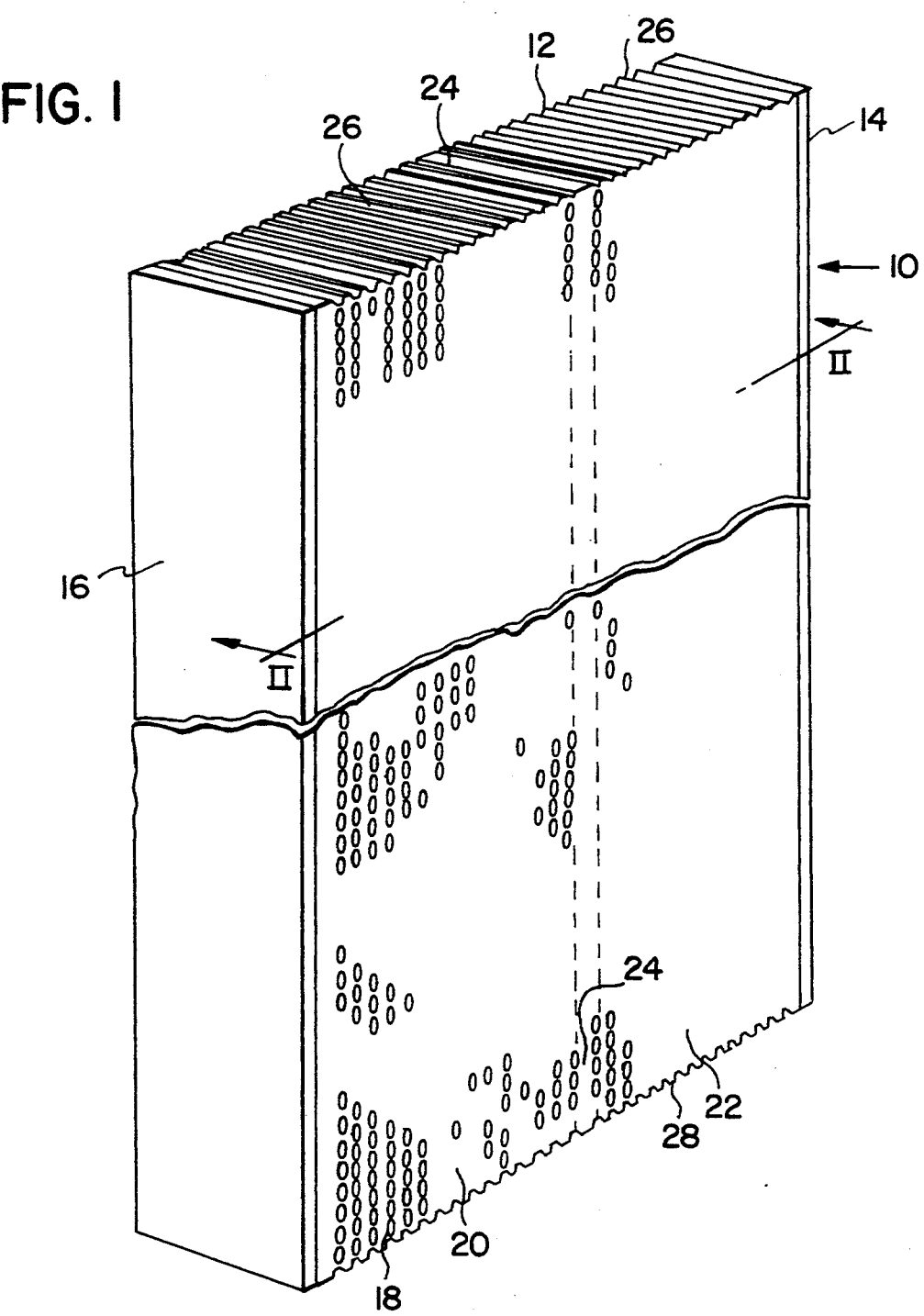
FIG. 1 is a perspective view of an embodiment of the invention.
Figure 2:
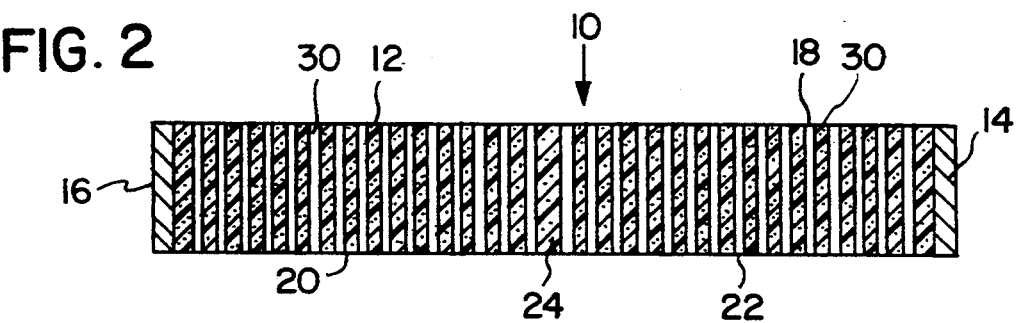
FIG. 2 is a sectional view of the embodiment of FIG. 1.
Figure 3:
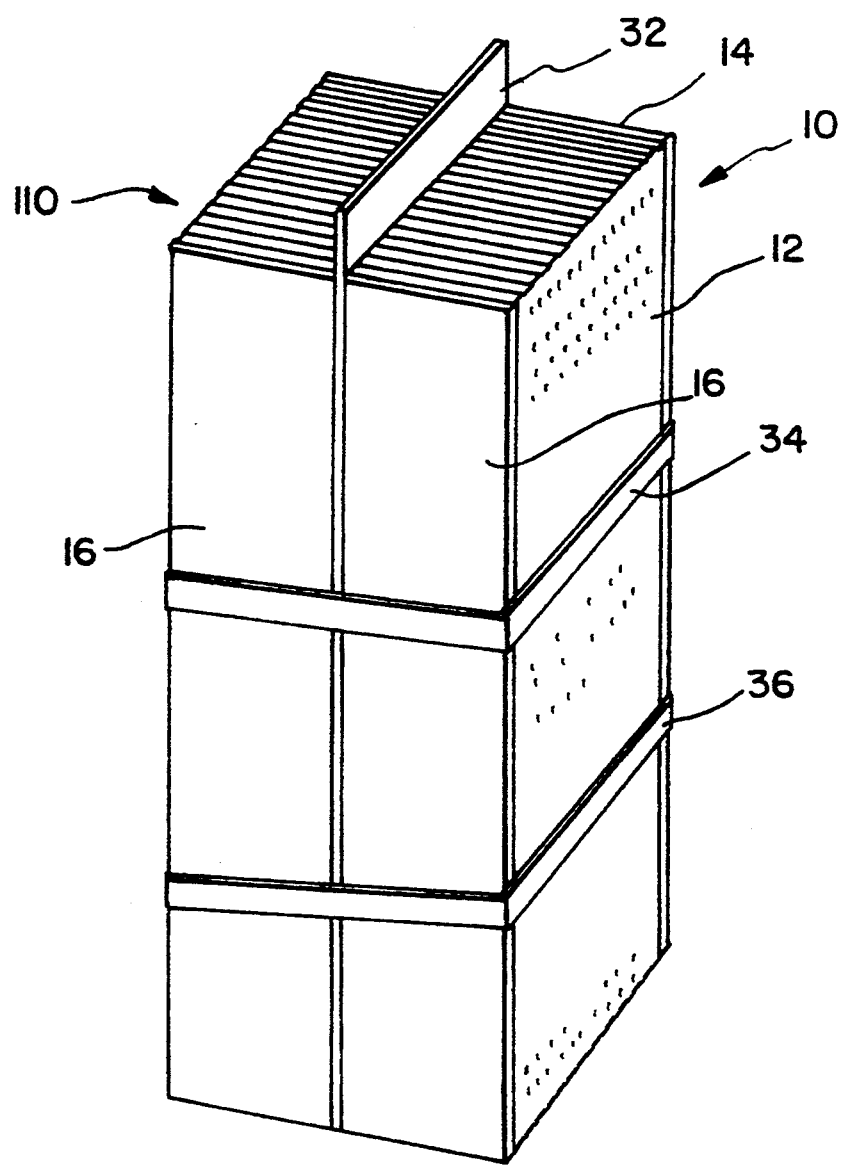
FIG. 3 is a perspective view of the embodiment of FIG. 1, in use.
Figure 4:
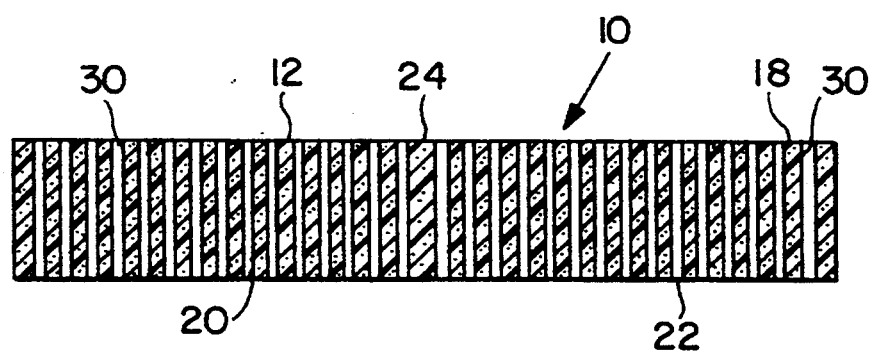
FIG. 4 is a sectional view of another embodiment of the invention.

The invention is now illustrated by reference to preferred embodiments thereof. The numeral 10 indicates a molded nest block of the invention. Nest block 12 has reinforcing side masonite panels 14 and 16. Bee holes 18 form two subarrays 20 and 22 separated by intervening space 24. End half holes 26 and 28 give a corrugated appearance to the block ends. As shown (FIGS. 2 and 4), holes 18 extend through block forming tubes 30. In use two nest blocks 10, and 110, slightly less than 4 feet long, are placed back to back against masonite board 32, somewhat more than 4 feet long, and are then strapped together by straps 34 and 36. The upper part of board 32 is used to hang the nest assembly within a bee shelter, using conventional attachment and suspension means, so it does not contact the ground. When blocks 10 and 110 include tapered holes, the larger holes are placed inward against masonite board 32, with the smaller holes outward.

Block 10 may be manufactured and sold and used as shown (FIG. 4) without masonite side reinforcing panels being present.

Applicant considers a four foot long block about the optimum size in practice.

As those skilled in the art would realize these preferred described details and processes can be subjected to substantial variation, modification, change, alteration, and substitution without affecting or modifying the function of the described embodiments. Although embodiments of the invention have been described above, it is not limited thereto, and it will be apparent to persons skilled in the art that numerous modifications and variations form part of the present invention insofar as they do not depart from the spirit, nature and scope of the claimed and described invention.

I claim:

1. A cocoon strippable molded leaf cutter bee nest block, formed of expanded plastic beads, having opposed sides, opposed ends, and opposed faces, having round integrally molded bee holes extending from one opposed face to the other, said holes tapering from a larger diameter in one said opposed face to a lesser diameter in said other opposed face.

2. A nest block of claim 1, wherein said larger diameter is about ¼ inch and said lesser diameter is about 15/64 inch.

3. A nest block of claim 2, having said opposed sides reinforced by attached panels.

4. A nest block of claim 1, formed of expanded polystyrene beads.

5. A nest block of claim 1, having said opposed sides reinforced by attached panels.

6. A nest block of claim 1, having a density of at least about 2 pounds/cubic foot.

7. A nest block of claim 1, comprising more than 1500 integrally molded bee holes.

8. A nest block of claim 1, comprising from about 1500 up to about 3600 integrally molded bee holes.

9. A cocoon strippable molded leaf cutter bee nest block, formed of expanded plastic beads, having opposed sides, opposed ends, and opposed faces, having round integrally molded bee holes extending from one opposed face to the other, said holes tapering from a larger diameter in one said opposed face to a lesser diameter in said other opposed face, said block having standard depth of between about 3 and 4 inches, standard width of about 12 inches and length of about 48 inches length, to accommodate about 3600 round bee holes and 60 end half holes in about 120 rows, said holes extending from one opposed face to the other, each said row containing 30 holes, said rows of said half holes forming recesses in said block ends.

10. A nest block of claim 9, wherein said opposed sides are reinforced by attached reinforcing panels.

11. A nest block of claim 10, having bee holes tapering from a larger diameter of about ¼ inch in one said opposed face to a lesser diameter of about 15/64 inch in said other opposed face, said reinforcing panels being masonite, said plastic being expanded polystyrene having a density of at least about 2 pounds/cubic foot.

* * * * *